United States Patent [19]

Chabrier de Lassauniere et al.

[11] Patent Number: 6,063,807
[45] Date of Patent: May 16, 2000

[54] CYCLO-OXYGENASE INHIBITOR AND AMIDINE DERIVATIVES SALTS, PREPARATION METHOD THEREFOR, USE THEREOF AS DRUGS, AND PHARMACEUTICAL COMPOSITIONS CONTAINING SAID SALTS

[75] Inventors: Pierre Etienne Chabrier de Lassauniere, Paris; Colette Broquet, Boulogne, both of France

[73] Assignee: Societe de Conseils de Recherches d'Applications Scientifiques (S.C.R.A.S.), France

[21] Appl. No.: 08/981,682

[22] PCT Filed: Jul. 15, 1996

[86] PCT No.: PCT/FR96/01095

§ 371 Date: Jan. 6, 1998

§ 102(e) Date: Jan. 6, 1998

[87] PCT Pub. No.: WO97/03678

PCT Pub. Date: Feb. 6, 1997

[30] Foreign Application Priority Data

Jul. 15, 1995 [GB] United Kingdom .................. 9514518

[51] Int. Cl.$^7$ ........................ A61K 31/40; C07D 209/26; C07D 333/22; C07C 323/02

[52] U.S. Cl. ........................ 514/420; 514/423; 548/500; 549/77; 549/499; 562/428; 562/439; 558/414

[58] Field of Search ............................ 558/414; 548/500; 562/428, 439; 549/77, 499; 514/420, 423

[56] References Cited

U.S. PATENT DOCUMENTS 4,324,801  4/1982  Matsuzaki et al. ..................... 424/311

FOREIGN PATENT DOCUMENTS 2263111  7/1993  United Kingdom .

OTHER PUBLICATIONS

Patent Abstracts of Japan JP61143320 (1 page) Jul. 1, 1986, Akinori et al.
Patent Abstracts of Japan (1 page) JP56147761 Nov. 16, 1981, Akinori et al.

*Primary Examiner*—Johann Richter
*Assistant Examiner*—Ebenezer Sackey
*Attorney, Agent, or Firm*—Bierman, Muserlian and Lucas

[57] ABSTRACT

Cyclo-oxygenase inhibitor and amidine derivative salts, preparation methods therefor, pharmaceutical compositions containing said salts and the use thereof particularly as NO synthase and cyclo-oxygenase inhibitors, are disclosed.

9 Claims, No Drawings

CYCLO-OXYGENASE INHIBITOR AND AMIDINE DERIVATIVES SALTS, PREPARATION METHOD THEREFOR, USE THEREOF AS DRUGS, AND PHARMACEUTICAL COMPOSITIONS CONTAINING SAID SALTS

This appln is a 371 of PCT/FR96/01095 filed on Jul. 15, 1996.

The present invention concerns novel compounds exhibiting dual biological activity, namely the simultaneous inhibition of the formation of nitrogen monoxide (NO) as well as the cyclo-oxygenase activity, a procedure for their preparation, pharmaceutical compositions comprising them and their use notably as inhibitors of NO synthase and cyclo-oxygenase.

The cyclo-oxygenase inhibitors or the medications analogous to asprin, for example acetylsalicylic acid and salicylic acid, the methyl indoline derivatives, such as indometacine (DCI of [1-(4-chlorobenzoyl)-5-methoxy-2-methyl-1H-indole-3-yl] acetic acid and sulindac (DCI of [5-fluoro-2-methyl-1-[[4-(methylsulfinyl)phenyl]-methylene-1H-indene-3-yl] acetic acid, the derivatives of the N-phenylanthranilic acids (meclofenamate, fenamates), the derivatives of propionic acid such as ibuprofen (DCI of p-isobutylhydratropic acid), naproxyn, fenoprofen, are widely used and have proved themselves sufficiently as efficacious medications in the treatment of inflammation, however, with several undesirable secondary effects at increased doses (R. Flower, S. Moncada and J. Vane, Mechanism of action of asprin-like drugs—In the pharmacological basis of therapeutics Goodman and Gilman, 1985, 29, 674–715). Moreover, these compounds were used at the same time in the acute and prophylactic treatment of migraines. The value of these medications is undeniable, even though their therapeutic responses are often incomplete and, in certain patients, the treatment with such compounds is not appropriate. Because of their anti-inflammatory and antiplatelet aggregate properties, these compounds are used as well for thrombosis with an evident reduction of edema, in the ischemic models of the brain and consequently are proposed in the treatment and the prevention of infarctions, concussions, and cerebrovascular diseases (W. Armstrong Recent trends in research and treatment of stroke, SCRIP, PJB Publications, 1991).

The biological activity of the NO-synthase inhibitors has only been recently discovered and their potential therapeutic function is only now in the investigative stage. These substances, in which the structures are represented by analogues of L-arginine and described in the Danish Patent 3041/90, are inhibitors of nitric oxide (NO) production. Our current knowledge of NO was revised in 1991, by Monacada et al., (S. Monacada, R. M. J. Palmer, E. A. Higgs: Nitric oxide: physiology, pathophysiology and pharmacology—Pharmacological reviews 43, 2, 109–142) and more recently by Kerwin et al. (Kerwin J., Lancaster J., Feldman P., Nitric oxide: a new paradigm for second messengers, J. Med. Chem. (1995), vol 38, 22, 4343–4362). In summary, it appears that NO serves as a transduction mechanism for soluble guanylate cyclase in platelets, the nervous system, and as effector molecule in immunological reactions in many cells and tissues, comprising macrophages and neutrophiles. NO is produced enzymatically from L-arginine by an enzyme called NO synthase. This enzyme exists in two forms: one constitutive (endothelial and neuronal) and the other inducible. In certain pathologies excessive production of NO can occur, as has already been demonstrated to occur in the course of a shock, and such as has already been described in the previously cited patent. In this context, the NO synthase inhibitors are medications effective in preventing the vascular consequences and mortality caused by an illness, particularly when they are combined with cyclo-oxygenase inhibitors such as asprin, indometacine or meclofenamate.

The beneficial effects of the combination of two active ingredients in the same molecule are open to occur for patients suffering from other pathologies, such as for example:

cardiovascular and cerebrovascular disorders comprising for example atherosclerosis, migraine, arterial hypertension, septic shock, cardiac or cerebral infarctions of ischemic or hemorragic origins, ischemias and thrombus;

peripheral or central nervous system disorders such as for example neurodegenerative illnesses where notably cerebral infarctions, senile dementias, including Alzheimer's disease, Huntington's chorea, Parkinson's disease, Creutzfeld Jacob's disease, lateral amyotrophic sclerosis but also pain, cerebral or spinal cord trauma, addiction to opiates, to alcohol and to substances inducing tolerance, erection and reproduction disorders, cognitive disorders or encephalopathies, may be cited;

proliferative and inflammatory diseases such as for example atherosclerosis, pulmonary hypertension, glomerulonephritis, portal hypertension, psoriasis, rheumatoid arthritis and arthrosis, fibrosis, amyloidosis, inflammation of the gastrointestinal system (colitis, Crohn's disease) or of the pulmonary system and inflammation of the air passages (asthma, sinusitis);

organ transplants;

auto-immune and viral diseases such as for example lupus, AIDS, parasitic and viral infections, diabetes, plaque sclerosis;

cancer; or all pathologies characterized by production or disfunctioning of NO and/or cyclo-oxygenases.

The invention has thus as object general formula I products $$A B \quad\quad (I)$$

in the form of a salt, in which

A represents a cyclo-oxygenase inhibitor presenting a carboxy function;

B represents a compound of general formula $I_B$

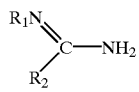

$$I_B$$

in which $R_1$ represents H, the nitro or phenyl radical, the phenyl radical potentially being substituted by one or more substituents chosen from among the halo, cyano, nitro, trifluorornethyl, lower alkyl or lower alkoxy radicals;

$R_2$ represents a lower alkyl radical; lower alkylthio; alkylthioalkyl; aryl potentially substituted by one or more substituents chosen from among the halo, cyano, nitro, trifluoromethyl, lower alkyl or lower alkoxy radicals; or amino potentially substituted by a radical chosen from among the nitro, amino, lower alkyl or phenyl radicals, the phenyl radical itself potentially being substituted by one or more substituents chosen from among the halo, cyano, nitro, trifluoromethyl, lower alkyl or lower alkoxy radicals;

and when A represents acetylsalicylic acid and $R_1$ a hydrogen atom, then $R_2$ represents neither an aryl radical nor a phenylamino radical, the phenyl radical potentially being substituted.

In the definitions indicated above, the term halo represents the fluoro, chloro, bromo or iodo radical, preferably fluoro or chloro.

The expression lower alkyl represents preferably a linear or branched alkyl radical comprising from 1 to 6 carbon atoms and in particular an alkyl radical comprising from 1 to 4 carbon atoms such as the methyl, ethyl, propyl, isopropyl, butyl, isobutyl, sec-butyl and tert-butyl radicals. The lower alkoxy radicals may correspond to the alkyl radicals indicated above. The methoxy, ethoxy or isopropyloxy radicals are preferred.

The expression aryl represents an aromatic radical, comprised of one condensed cycle or several condensed cycles; each cycle may potentially contain one or more identical or different heteroatoms chosen from among sulfur, nitrogen or oxygen. Examples of the aryl radical are the phenyl, naphtyl, thienyl, furyl, pyrrolyl, imidazolyl, pyrazolyl, isothiazolyl, thiazolyl, isoxazolyl, oxazolyl, pyridyl, pyrazinyl, pyrimidyl, benzothienyl, benzofuryl and indolyl radicals.

The invention has more particularly as its object products of general formula I such as defined above, characterized in that compound A is chosen from among the salicylates such as salicylic acid and its salt derivatives, indometacine, sulindac, fenamates and derivatives of propionic acid.

Among the derivatives of salicylic acid may be cited compounds obtained by esterification of the carboxy function of salicylic acid such as, for example, methyl salicylate, compounds obtained by substitution of the hydroxy radical of salicylic acid, for example, acetylsalicylic acid or even compounds obtained by the addition of substituent(s) on the free sites of the phenyl radical or salicylic acid such as for example, diflunisale. Among the fenamates, mefenamic acid, meclofenamic acid, flufenamic acid and tolfenamic acid may all be cited. Examples of derivatives of propionic acid may be cited to be compounds such as ibuprofen, naproxyn, fenoprofen, fenbufen, flurbiprofen, indoprofen, ketoprofen or supropfen.

The invention has particularly as its object compounds of general formula I such as have been described above, characterized in that A represents salicylic acid, methyl salicylate, acetylsalicylic acid, indometacine, sulindac, mefenamic acid, meclofenamic acid or ibuprofen; and B is of general formula ($I_B$) such as has been defined above in which $R_1$ represents H, the nitro or phenyl radical, the phenyl radical potentially being substituted by one or more substituents chosen from among the chloro, fluoro, cyano, nitro, trifluoromethyl, methyl, ethyl, methoxy, ethoxy or isopropyloxy radicals; and $R_2$ represents an amino radical; hydrazino; nitroamino; methylamino; ethylamino; methyl; ethyl; methylthio; methylthiomethyl; phenyl potentially substituted by one or more substituents chosen from among the chloro, fluoro, cyano, nitro, trifluoromethyl, methyl, ethyl, methoxy, ethoxy or isopropyloxy radicals; thienyl; furyl or pyrrolyl.

More particularly, the invention has as object products described below in the examples, in particular products corresponding to the following formulas;

aminoguanidinie salicylate;

aminoguanidine ibuprofenate;

aminoguanidine indomethacinate;

methylguanidine acetylsalicylate;

methylguanidine salicylate;

methylguanidine ibuprofenate;

methylguanidine mefenamate.

The invention has equally as its object a procedure for the preparation of products of general formula I such as defined above, characterized in that a mixture of formula A compounds such as defined above is allowed to react in water at a temperature between ambient temperature and 7° C. with a formula B compound such as defined above.

At the time of the start of the procedure, the formula A compound may be used as is or in the form of a salt such as, for example, the sodium salt. As well, the formula B compound may be used as is or in the form such as, for example, its bicarbonate or its hydrochloride.

The formula A products are known and may be fabricated by the methods known by persons skilled in the art. The formula B products may be obtained in applying the preparation methods of amidines known by persons skilled in the art (Schwan T. J. et al., J. Pharm. Sci. (1975), 64, 337–338; Roger R et al., Chem. Rev. 61, 179, (1961); Tetrahedron, 29(14), 2147–51 (1973); Patai S., Chem. Amidines Imidates, vol.1, 283–348 (1975); Patai S., Chem. Amidines Imidates, vol.2, 339–366 (1990)).

The compounds of the present invention possess interesting pharmacological properties. They present a dual biological activity, namely that they inhibit both the L-arginine/nitric oxide process and the cyclo-oxygenase process at the same time. The compounds of the present invention may thus be used in different therapeutic applications.

Taking into account the potential role of NO synthase and cyclo-oxygenase in physiopathology, the compounds according to the invention may produce beneficial and favorable effects in the treatment of:

cardiovascular and cerebrovascular disorders, including, for example, migraines, cerebral congestions, infarctions, ischemias, septic, endotoxic and hemorrhagic shocks, and pain;

diverse forms of inflammation, comprising, for example, acute rheumatic fevers, rheumatoid arthritis or other types of arthritis, osteoarthritis, asthma;

immune system disorders, comprising viral or non-viral infections, auto-immune diseases and all pathologies characterized by an excessive production of nitric oxide and/or arachidic acid metabolites.

An illustration of these pharmacological properties of the compounds of the invention may be found below in the experimental section.

These properties make the formula I products suitable for pharmaceutical use. The present application has as well as its object, as medications, formula I products such as defined above as well as the pharmaceutical compositions comprising, as an active ingredient, at least one of the medications such as defined above.

The invention concerns thus pharmaceutical compositions comprising a compound of the invention, in association with a pharmaceutically acceptable medium. The pharmaceutical composition may be in the form of a solid, for example, powders, granules, tablets, capsules or suppositories. The appropriate solid mediums may be, for example, calcium phosphate, magnesium stearate, talc, sugars, lactose, dextrine, amidon, gelatin, cellulose, methyl cellulose, sodium carboxymethyl cellulose, polyvinylpyrrolidine and wax.

The pharmaceutical compositions comprising a compound of the invention may also be in the form of a liquid, for example, solutions, emulsions, suspensions or syrups. The appropriate liquid mediums may be, for example, water, organic solvents such as glycerol or glycols, as well as their mixtures, in various proportions, in water, added to pharmaceutically acceptable oils or fats. The pharmaceutical compositions according to the invention may be administered according to the classic methods of administration such as oral administration or by intramuscular injection, intraperitoneal, intravenous or subcutaneous injections.

The invention has as well as its object the use of formula I products such as defined above, for the preparation of medications intended for the treatment of cardiovascular or cerebrovascular disorders, medications intended for treatment of diverse inflammations, medications intended for the treatment of immune system disorders.

The following examples are presented to illustrate the above procedures and in no case are to be considered as limiting the scope of the invention.

EXPERIMENTAL SECTION

EXAMPLE 1
Aminoguanidine Salicylate 420 mg (2.5 mmol) aminoguanidine bicarbonate are dissolved in 25 ml water by heating to 70° C., subsequently, while agitating, an aqueous solution of 400 mg of sodium salicylate is added. The mixture is heated for 20 minutes then lyophilized (white powder; m.p.=148° C.).

EXAMPLE 2
Aminoguanidinie Ibuprofenate 420 mg (2.5 mmol) aminoguanidine bicarbonate are dissolved in 25 ml water by heating to 70° C. An aqueous solution of 570 mg of sodium ibuprofen is added. The mixture is heated for 20 minutes then lyophilized (white powder ; m.p.=134° C.).

EXAMPLE 3
Aminoguanidine Indomethacinate

Proceed as described in example 1 but substituting indomethacine in place of sodium salicylicate (yellow powder; m.p.=196° C.).

EXAMPLE 4
Methylguanidine Acetylsalicylate 450 mg (2.5 mmol) acetylsalicylic acid are dissolved in 20 ml water containing 2.5 ml of 1N NaOH. Next 237.8 mg methylguanidine chlorohydrate in 10 ml water is added. The mixture is agitated for 15 minutes. A clear solution is obtained. Lyophilizationfurnishes a white powder (m.p.= 153° C.). NMR-$^1$H (100 MHz, $D_2O$): 7.3–6.6 (m, 4H, aromatic); 2.3 (s, 3H, $NCH_3$); 1.8 (s, 3H, $COCH_3$).

EXAMPLE 5
Methylguanidine Salicylate 345 mg (2.5 mmol) salicylic acid is dissolved while hot in 20 ml water containing 2.5 ml of 1N NaOH. A solution of methylguanidine chlorohydrate (2.5 mmol) in 10 ml water is added. The mixture is agitated at 40° C. for 10 minutes. Lyophilization furnishes a highly voluminous white powder (m.p.=140° C.).

NMR-$^1$H (100 MHz, $D_2O$): 7–6.8 (m, 4H, aromatic); 2.4 (s, 3H, $NCH_3$).

EXAMPLE 6
Methylguanidine Ibuprofenate

While hot, 2.5 mmol ibuprofen are dissolved in 20 ml water containing 2.5 ml of 1N NaOH. A solution of methylguanidine chlorohydrate (2.5 mmol) in 10 ml water is added, followed by agitating at 60° C. for 15 minutes. Lyophilization furnishes a white powder (m.p.=174° C.).

NMR-$^1$H (100 MHz, $D_2O$): 7.2 (s, 4H, aromatic); 3.4 (q, 1H, $C_6H_6$—C$\underline{H}$(Me)—CO); 2.6 (s, 3H, $NCH_3$); 2.25 (d, 2H, C$\underline{H}_2C_6H_6$); 1.6 (m, 1H, C$\underline{H}(CH_3)_2$); 1.2 (d, 3H, —CH($CH_3$)—$CO_2H$); 0.8 (d, 6H, $2CH_3$).

EXAMPLE 7
Methylguanidine Mefenamate

Proceed as described in example 6, but by substituting mefenamic acid in the place of ibuprofen. Upon chilling, the compound precipitates. Filter and dry the product (m.p.= 124° C.).

NMR-$^1$H (100 MHz, $D_2O$): 8.1 (m, 1H, H in o of $CO_2H$); 7.2–6.8 (m, 6H, $2C_6H_6$); 2.9 (s, 3H, $NCH_3$); 2.4 and 2.3 (d, $2CH_3C_6H_6$).

Using the procedure indicated above, the following products may be prepared which: are as well a part of the invention and which comprise the preferred products:

TABLE 1

| Com- | | B | |
| pound | A | $R_1$ | $R_2$ |
| --- | --- | --- | --- |
| C | salicylic acid | nitro | hydrazino |
| D | salicylic acid | H | methylamino |
| E | salicylic acid | 2-fluorophenyl | amino |
| F | acetylsalicylic acid | 4-methoxyphenyl | ethyl |
| G | acetylsalicylic acid | nitro | ethoxy |
| H | methyl salicylate | 3-chlorophenyl | methyl |
| I | methyl salicylate | H | hydrazino |
| J | indometacine | 3,4-dichlorophenyl | propyl |
| K | indometacine | 4-methylphenyl | hydrazino |
| L | indometacine | H | methylamino |
| M | indometacine | nitro | ethylamino |
| N | indometacine | nitro | 3-chlorophenyl |
| O | sulindac | 3-cyanophenyl | amino |
| P | sulindac | H | methylamino |
| Q | sulindac | H | hydrazino |
| R | mefenamic acid | H | amino |
| S | mefenamic acid | H | thienyl |
| T | mefenamic acid | nitro | hydrazino |
| U | meclofenamic acid | nitro | amino |
| V | meclofenamic acid | 3-trifluorophenyl | isopropyloxy |
| W | ibuprofen | H | methylthiomethyl |
| X | ibuprofen | nitro | methyl |
| Y | ibuprofen | nitro | furyl |

Pharmacological Studies of the Products of the Invention

The compounds of the invention were subjected to in vitro biological tests, in order to prove their activity in blocking inducible NO synthase and cyclo-oxygenase. They were compared to the reference substances such as aminoguanidine, L-nitroarginine, ibuprofen, indometacine, acetylsalicylic acid.

1) In vitro Effect on Inducible NO Synthase of J774A1 Murine Macrophages

The test consists of measuring the conversion of L-arginine to L-citrulline by NO synthase according to the Bredt and Snyder method (Proceedings of the National Academy of Sciences USA, 682–685, 1990). The J774A1 murine macrophages produce a large quantity of NO after activation by lipopolysaccharides (LPS) and interferon-γ (IFN-γ). The cells are cultivated in DMEM (Dulbecco's Modified Eagle's Medium) enriched with 10% fetal calf serum at 37° C. in an atmosphere of 5% $CO_2$ after activation by LPS and IFN-γ. They are seeded in 150 cm² flasks at the rate of 5000 cells/cm². The incubation is carried out in the presence of LPS (1 μg/ml) and murine IFN-γ (50 U/ml) in DMEM enriched with 10% fetal calf serum. The NO synthase is isolated with an extraction buffer (HEPES 50 mM, pH 7.4, dithiothreitol 0.5 mM, pepstatin A 1 mg/ml, leupeptine 1 mg/ml, soy bean trypsin inhibitor 1 mg/ml, antipaine 1 mg/ml and PMSF 10 mg/ml). After sonication in the extraction buffer at 4° C., the homogenates are ultra-centrifuged (100,000 g at 4° C. for 1 hour).

The dosage is performed in glass test tubes in which 100 μl of incubation buffer comprising 100 mM HEPES, pH 7.4, 1 mM dithiotreitol, 2.5 mM of $CaCl_2$, 10 μM tetrahydrobiopterine, FAD 10 μM, BSA 1 mg/ml, 2 mM reduced NADPH, 2 mM EDTA and 2.5 mM $CaCl_2$ is distributed. 25 μl of a solution comprising 100 nM tritiated arginine (specific activity: 56.4 Ci/mmole, Amersham) and 40 μM non-radioactive arginine are added. The reaction is initiated by adding 50 μl of homogenate, the final volume being 200 μl (the remaining 25 μl being either water, or the product to be tested). After 15 minutes, the reaction is stopped with 2 ml stop buffer (20 mM HEPES, pH 5.5, 2 mM EDTA). After placing the samples onto a column of 1 ml DOWEX resin, the radioactivity is quantified by a liquid scintillation spectrometer.

The results are expressed as value of $CI_{50}$ and are summarized in the table of paragraph 2 (first column entitled "inducible NO synthase, formation of citrulline").

2) In vitro Effect on the Production of Nitrites by J774A1 Murine Macrophates

This test is used to measure the inhibiting activity of the products on inducible NO synthase of the cells in culture. The cells are cultivated in a DMEM medium (Dulbecco's Modified Eagle Medium) enriched with 10% fetal calf serum at 37° C. under an atmosphere of 5% $CO_2$. For these experiments, they are separated into 96 well plaques (50,000 cells per well) and incubated in DMEM without phenol red at 10% fetal calf serum with LPS (1 μg/ml) and murine IFN-γ (50 U/ml) in the presence or absence of the product to be tested. After 48 hours, the nitrite concentration in the culture medium, products of the degradation of NO, is measured calorimetrically according to Green et al., Analytical Biochemistry 126, 131–138 (1982). The results are expressed in the value of $CI_{50}$ in the table of paragraph 2 (second column of results entitled "inducible NO synthase, formation of nitrites").

| Products | $CI_{50}$ (μM) | |
|---|---|---|
| | inducible NO synthase (formation of citrulline) | inducible NO synthase (formation of nitrites) |
| Aminoguanidine | 20 | 22 |
| L-nitroarginine | 21 | 100 |
| Ibuprofen | inactive | inactive |
| Indometacine | inactive | inactive |
| Example 2 | 11 | 16 |
| Example 3 | 26 | 33 |

3) In vitro Effect on Nitrite and PGE2 Production by Rat Microglial Cells

The microglial cells are isolated from cultures of glial cells derived from the cortex of neonatal Wistar rats according to the protocol developed by Thery et al. (1991). The microglial cells are seeded in 24 well plaques at a rate of $5.10^5$ cells per ml and 0.5 ml per well. The microglial cells are incubated in the presence of LPS (10 μg/ml) and inhibitors for 24 hours at 37° C. in an atmosphere of 5% $CO_2$. After 24 hours, the supernatants are removed in order to measure the nitrite and $PGE_2$ concentrations. $PGE_2$ is dosed with the help of commercial radioimmunological dosage by NEN according to the operating method described by the manufacturer. Each sample is dosed in duplicate. The results are expressed as $CI_{50}$ calculated with the help of a linear regression on the linear sectors of the inhibition curve (FigP6C software). The nitrites are dosed according to the method by Green et al. (Analytical Biochemistry 126, 131–138, 1982). The results are expressed in the form of $CI_{50}$ and are indicated in the table below for example 2.

| Product | Nitrite Production $CI_{50}$ (μM) | $PGE_2$ Production $CI_{50}$ (μM) |
|---|---|---|
| Example 2 | 97 ± 35 | 3.1 ± 1.9 |
| Aminoguanidine | 109 ± 44 | inactive |
| Ibuprofen | inactive | 1.3 ± 0.22 |

4) In vitro Effect on Inducible Cyclo-oxygenase

Cyclo-oxygenase exists in two isoforms, COX-1 (constitutive) and COX-2 induced by the mitogen, cytokine and endotoxin inflammatory agents. The compounds were tested on the enzymatic activity of these two semipurified isoforms.

The principle of the test is the quantification of the conversion of arachidonic acid (AA) to $PGE_2$ by COX-1 or COX-2. The method is suggested by Futaki et al. (Prostaglandins, 47, 55–59, 1994). COX-1 (Prostaglandin H synthase-1, EC 1.14.9.1) is conserved at −80° C. and are derived from seminal vesicles of ram. COX-2 (Prostaglandin H synthase-2) is also conserved at −80° C. and are derived from ewe placenta.

The tubes are filled with 500 μl of buffer (100 mM of Tris HCl, pH 8, 1 μM hematine, 1 mM phenol) and the compounds of the invention or the reference substances in concentrations ranging from 1 nM to 1 mM. The controls consist of buffer without inhibitors. After 2 minutes incubation with 5U (COX-2) or 10U (COX-1) enzyme, 5 μl arachidonic acid at 10 μM are added for 2 minutes. The reaction is stopped with 1N 30 μl HCl. The extraction is performed on Seppack C18 columns (Waters). After evaporating till dry, $PGE_2$ is measured by radioimmunological dosage from a commercial kit. The results are expressed as value of $CI_{50}$ and are summarized in the table below.

| Products | $CI_{50}$ (μM) | |
|---|---|---|
| | COX-1 | COX-2 |
| Acetylsalicylic acid | 77.8 | 648 |
| Salicylic acid | >1000 | >1000 |
| Mefenamic acid | 83.9 | 388 |
| Ibuprofen | >1000 | >1000 |
| Indometacin | 0.54 | 15.9 |
| Aminoguanidine | >1000 | >1000 |
| L-nitroarginine | >1000 | >1000 |
| Example 2 | 459 | 525 |
| Example 3 | 0.108 | 29.4 |
| Example 4 | 243 | >1000 |
| Example 5 | >1000 | >1000 |
| Example 6 | >1000 | >1000 |
| Example 7 | 411 | 331 |

We claim:

1. A compound of the formula

A B            (I)

in the form of non-toxic salt, wherein

A is a cyclo-oxygenase inhibitor presenting a carboxy function;

B is

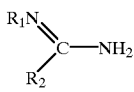

$R_1$ is selected from the group consisting of hydrogen, nitro and phenyl optionally substituted by one or more members selected from the group consisting of cyano, nitro, trifluoromethyl, lower alkyl and lower alkoxy, $R_2$ is selected from the group consisting of a) lower alkyl, lower alkylthio, alkylthioalkyl, aryl optionally substituted by one or more substituents selected from the group consisting of halo, cyano, nitro, trifluoromethyl, lower alkyl and lower alkoxy and b) amino optionally substituted by a member selected from the group consisting of nitro, amino, lower alkyl and phenyl optionally substituted by one or more substituents selected from the group consisting of halo, cyano, nitro, trifluoromethyl, lower alkyl and a lower alkoxy, with the proviso that when A is acetylsalicylic acid and $R_1$ is a hydrogen atom, then $R_2$ is neither an aryl nor an phenylamino optionally substituted.

2. A compound of claim 1, wherein

A is selected from the group consisting of salicylates, indometacine, sulindac, fenamates and propionic acid.

3. A compound of claim 1 wherein

A is selected from the group consisting of salicylic acid, methyl salicylate, acetylsalicylic acid, indometacine, sulindac, mefenamic acid, meclofenamic acid and ibuprofen; and $R_1$ is selected from the group consisting of H, nitro and phenyl optionally substituted by one or more substituents selected from the group consisting of chloro, fluoro, cyano, nitro, trifluoromethyl, methyl, ethyl, methoxy, ethoxy and isopropyloxy and $R_2$ is selected from the group consisting of amino, hydrazino; nitroamine; methylamino; ethylamino; methyl; ethyl; methylthio; methylthiomethyl; phenyl optionally substituted by one or more substituents selected from the group consisting of chloro, fluoro, cyano, nitro, trifluoromethyl, methyl, ethyl, methoxy, ethoxy, isoproplyloxy thienyl, furyl and pyrrolyl.

4. A compound of claim 1 selected from the group consisting of aminoguanidine salicylate;

aminoguanidine ibuprofenate;

aminoguanidine indomethacinate;

methylguanidine acetylsalicylate;

methylguanidine salicylate;

methylguanidine ibuprofenate; and methylguanidine mefanamate.

5. A process for the preparation of a compound of claim 1 comprising reacting a compound of formula A as defined in claim 1 in water at a temperature between ambient temperature and 70° C., with a compound of formula B as defined in claim 1.

6. A composition for inhibiting NO synthase and cyclooxygenase comprising an inhibiting effective amount of a compound of claim 1 and a pharmaceutical carrier.

7. A composition for inhibiting NO synthase and cyclooxygenase comprising an inhibiting effective amount of a compound of claim 4 and a pharmaceutical carrier.

8. A method of treating cerebrovascular and cardiovascular disorders in warm-blooded animals comprising administering to warm-blooded animals in need thereof an cerebrovascular and cardiovascular effective amount of a compound of claim 1.

9. A method of treating cerebrovascular and cardiovascular disorders in warm-blooded animals comprising administering to warm-blooded animals in need thereof an antiflammatorily and antiplatelet agglomerative effective amount of a compound of claim 4.

* * * * *